US00PP30977P3

(12) United States Plant Patent
Bally

(10) Patent No.: US PP30,977 P3
(45) Date of Patent: Oct. 29, 2019

(54) MANGO PLANT NAME 'NMBP 1201'

(50) Latin Name: ***Mangifera indica* L.**
Varietal Denomination: NMBP-1201

(71) Applicant: COMMONWEALTH SCIENTIFIC AND INDUSTRIAL RESEARCH ORGANISATION, Acton Act (AU)

(72) Inventor: Ian Stephen Edward Bally, Mareeba (AU)

(73) Assignee: Commonwealth Scientific and Industrial Research Organisation, Acton Act (AU)

( * ) Notice: Subject to any disclaimer, the term of this patent is extended or adjusted under 35 U.S.C. 154(b) by 0 days.

(21) Appl. No.: 15/731,850

(22) Filed: Aug. 16, 2017

(65) Prior Publication Data

US 2019/0059186 P1 Feb. 21, 2019

(51) Int. Cl.
*A01H 5/08* (2018.01)
*A01H 6/00* (2018.01)

(52) U.S. Cl.
USPC ..... Plt./159
CPC ..... *A01H 6/00* (2018.05); *A01H 5/08* (2013.01)

(58) Field of Classification Search
USPC ..... Plt./159
CPC ..... A01H 5/08; A01H 6/00
See application file for complete search history.

(56) References Cited

PUBLICATIONS

Brown et al. Mango growers want new varieties now. ABC Rural 2013, retrieved on Jul. 25, 2018, retrieved from the Internet at http://www.abc.net.au/site-archive/rural/news/content/201302/s3694462.htm, 3 pp. (Year: 2013).*

Plant Varieties Journal Official Journal of Plant Breeder's Rights Office, IPAustralia, Quarter Three 2008, vol. 21, No. 3, pp. 1,32,42,88-89,290-296. (Year: 2008).*

Bally ISE, Kulkarni VJ, Johnson PR, Leonardi J, Robinson D, Harris MA, Hamilton D, (2000) The Australian National Mango Breeding Project. Acta Horticulturae, 509, 225-231.

Oliveri, L. "Growers wanted for trial" Rural Insight (Oct. 23, 2015), one page.

McConchie, C., "Deed to Transfer Rights for New Mango Cultivars Finalised", p. 7, "Top Paddock Newsletter" by Department of Primary Industry and Fisheries Northern Territory Government, Australia, Issue 54, downloaded from https://dpir.nt.gov.au/_data/assets/pdf_file/0010/227584/54-tp.pdf (Dec. 2015), Total 14 pp.

"New Varieties: Expression of Interest—mango growers" AMIA downloaded from https://www.industry.mangoes.net.au/resource-collection/2015/12/17/new-varieties-expressions-of-interestmango-growers (Dec. 18, 2015), 3 pp.

Brann, M. "Mango farms signing up to plant long-awaited new varieties" ABC Rural, downloaded from https://www.abc.net.au/news/rura1/2016-12-06/mango-farms-signing-up-to-plant-new-varieties/8080854 (Dec. 5, 2016), 3 pp.

Faichney, E. "Good things come to those who wait." AMIA, downloaded from https://www.industry.mangoes.net.au/resource-collection/2018/10/8/good-things-come-to-those-who-wait (Oct. 8, 2018), 3 pp.

Australian Plant Breeder's Rights Application No. 2008/250 accepted Sep. 16, 2008, PBR Certificate No. 3837, granted on Jun. 26, 2009, 9 pp.

"Mango Hybrid NMBP-1201" Department of Agriculture Fisheries and Forestry, National Mango Breeding Program, (Oct. 2012), 7 pp.

* cited by examiner

*Primary Examiner* — June Hwu
(74) *Attorney, Agent, or Firm* — Buchanan Ingersoll & Rooney PC

(57) ABSTRACT

A new and distinct variety of Mango plant, herein referred to by its cultivar name, 'NMBP-1201', is provided which forms fruit with an average weight of 361 grams with skin that is soft red to dark red blush over a yellow background in coloration. The new variety is an early to mid-season variety.

17 Drawing Sheets

Figure 1:
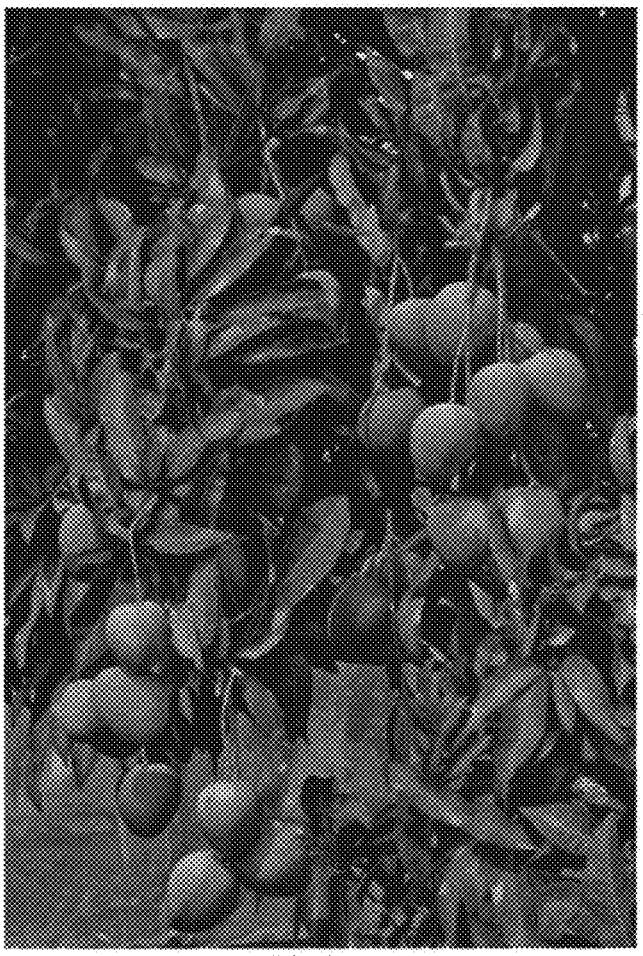

Botanical/commercial classification:
Latin name.—*Mangifera indica* L.
Common name—Mango Plant.
Varietal denomination: 'NMBP-1201'.

SUMMARY OF THE INVENTION

The new variety of *Mangifera indica* Mango plant of the present invention was created by closed pollination using hand pollination techniques in 1995 in Darwin, Northern Territory, Australia wherein two parents which previously had been studied were crossed in the hope that they would contribute the desired characteristics. The new cultivar was selected after comparative evaluation of tree and fruit characteristics over several seasons at two sites: Mareeba, Queensland and Darwin, Northern Territory in Australia. The female parent (i.e., seed parent) of the new variety was the 'Irwin' variety (non-patented). The male parent (i.e., pollen parent) was the 'Kensington Pride' variety (non-patented).

The parentage can be summarized as follows:

'Irwin' x 'Kensington Pride'.

The seeds resulting from the above pollination were sown. The new variety was grafted on the 'Kensington Pride' variety in early 1996 and field planted at Southedge research station, Queensland, Australia on Oct. 12, 1996. The candidate cultivar was selected after comparative evaluation of tree and fruit characteristics over several seasons. Selective study resulted in the identification of a single plant of the new variety.

It was found that the new Mango plant of the present invention possesses the following combination of characteristics:

(a) displays a medium vigor plant with a compact dense canopy,
(b) exhibits a medium to heavy yielding with a tendency for biennial bearing,
(c) is polyembryonic,
(d) has a harvest season that is early to mid-season, and
(e) provides a fruit with sweet Kensington Pride style flavor with a slight tang.

The new variety well meets the needs of the horticultural industry.

The new variety can be readily distinguished from its ancestors. More specifically, the 'Irwin' variety displays an erect main branch and the mature fruit has the presence of a neck, and the 'Kensington Pride' variety provides an obtuse shape of the leaf blade base and the mature fruit has the presence of sinus, whereas the new variety displays an intermediate to spreading attitude of the main branch, provides an acute shape of the leaf bade base, and the mature fruit of the new variety has no presence of a neck and no presence of sinus. Additionally, the new variety can be readily distinguished from other known cultivars. For example, the 'B74' variety (U.S. Plant Pat. No. 17,770) provides monoembryonic seed, while the new variety is polyembryonic; and the 'Tommy Atkins' variety (non-patented) displays fruit which matures late in the season, while the new variety has fruit that matures earlier in the season. Similarly, the 'Delta R2E2' variety (non-patented) displays fruit which matures mid to late season, while the new variety has fruit that matures earlier in the season, and has an average fruit weight greater than that of the new variety. Also, the 'NMBP-1243' variety (U.S. Plant patent application Ser. No. 15/731,843) displays leave with an obtuse base shape and an acute apex shape, whereas the new variety displays leaves with an acute base shape and an attenuate apex shape.

The new variety has been found to undergo asexual propagation in Australia by a number of routes, including by grafting of cuttings. The typical asexual propagation of the new variety has been to initially increase the numbers of trees for advanced trials and evaluation and more recently for supply of on-farm large scale trials of the variety. Propagation has been by Whip and Tongue or cleft grafting of the new variety (scion) on to a seedling rootstock of the variety 'Kensington Pride' in the Mareeba district of Queensland, Darwin in the Northern Territory, or Kununurra in Western Australia. Asexual propagation in Australia has shown that the characteristics of the new variety are stable and strictly transmissible by asexual propagation from one generation to another. Accordingly, the new variety undergoes asexual propagation in a true-to-type manner.

The new variety has been named 'NMBP-1201'.

BRIEF DESCRIPTION OF THE PHOTOGRAPHS

The accompanying photographs show, as nearly true as it is reasonably possible to make the same in color illustrations of this character, typical specimens of the new variety.

FIG. 1—illustrates specimens of branches with mature fruit on an eight year-old tree.

Figure 2:
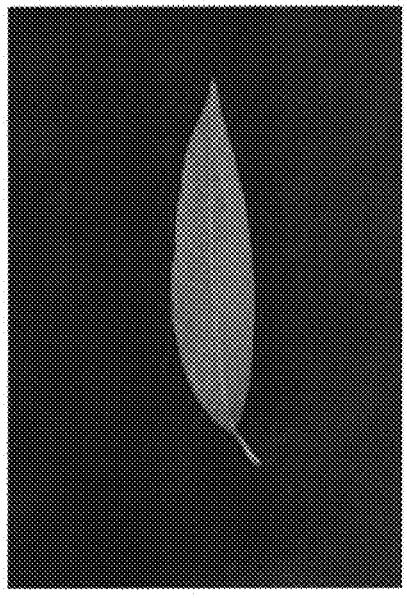

FIG. 2—illustrates a specimen of a mature leaf—upper surface.

Figure 3:
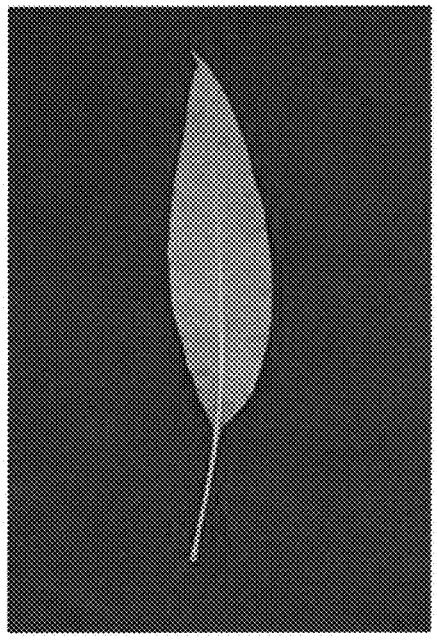

FIG. 3—illustrates a specimen of an immature leaf—lower surface.

Figure 4:
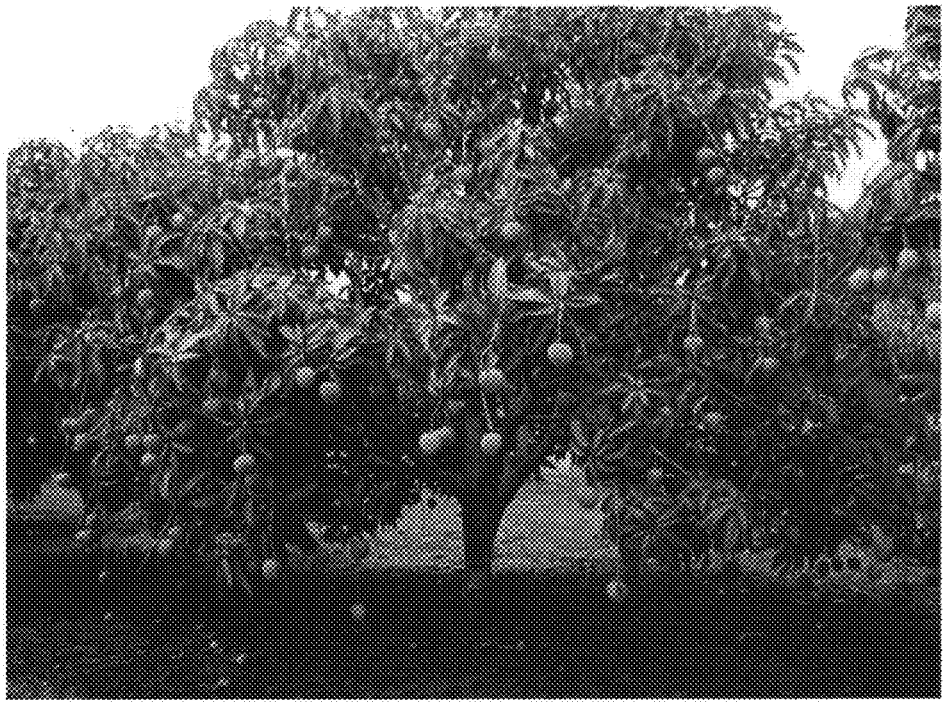

FIG. 4—illustrates a specimen of a six year-old single plant with mature fruit.

Figure 5:
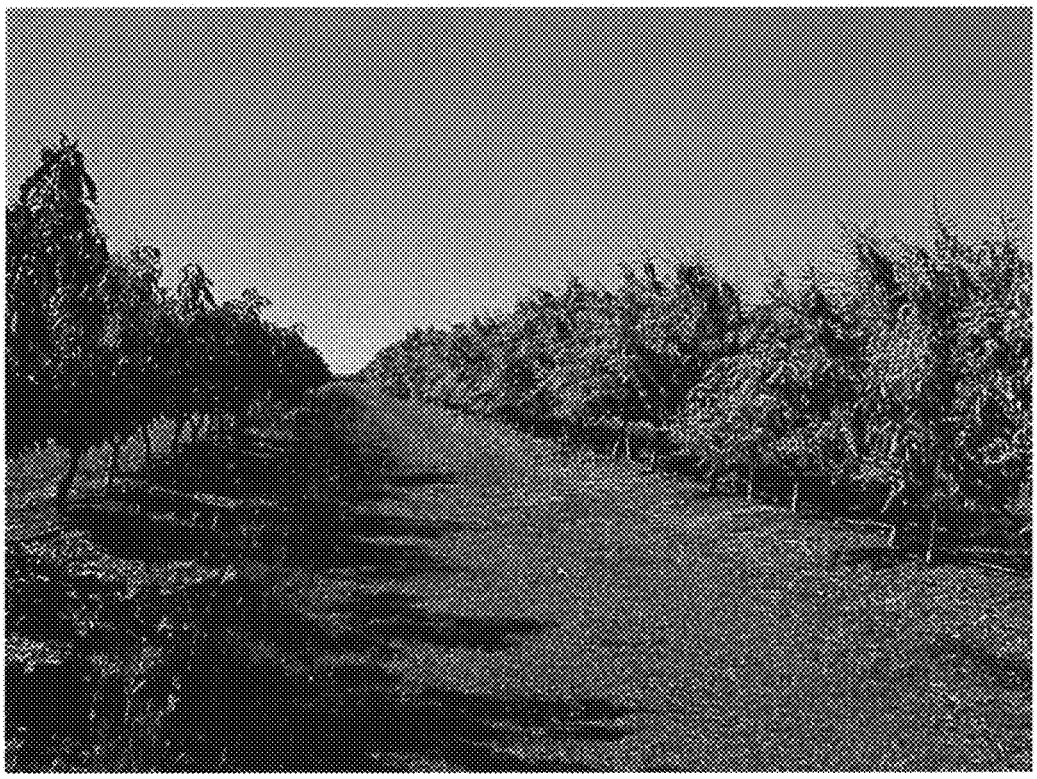

FIG. 5—illustrates specimens of multiple five year-old flowering plants.

Figure 6:
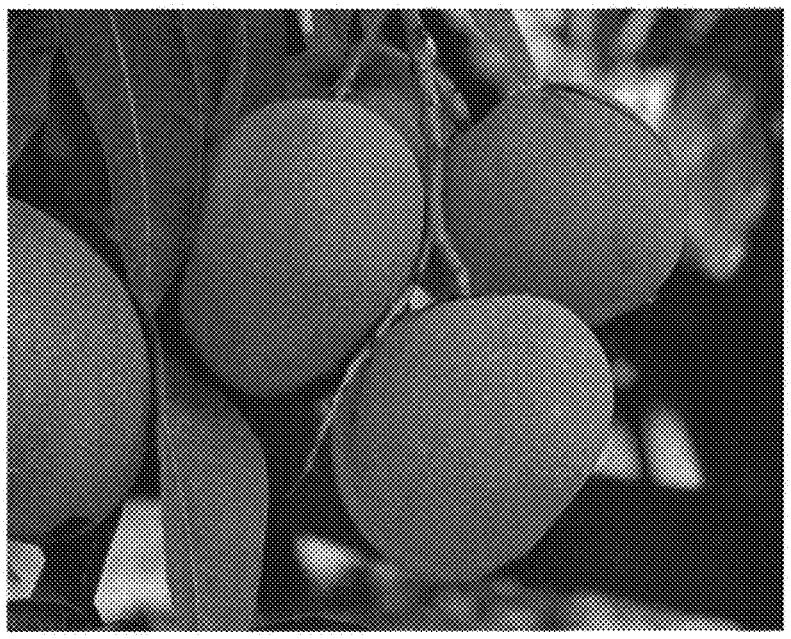

FIG. 6—illustrates specimens of multiple mature fruit growing on an inflorescence on a six year-old tree.

Figure 7:
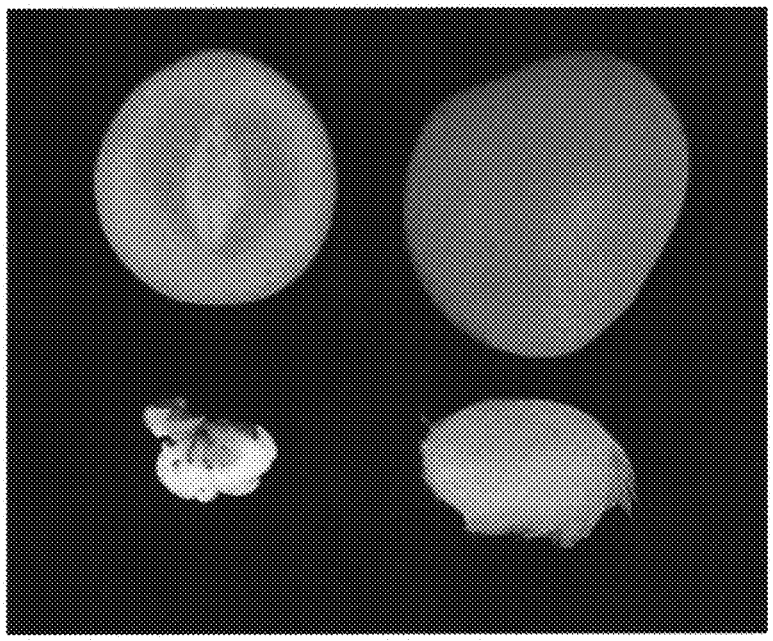

FIG. 7—illustrates a specimen of a ripe fruit, shown as whole and halved and illustrates a specimen of the endocarp and embryo.

Figure 8:
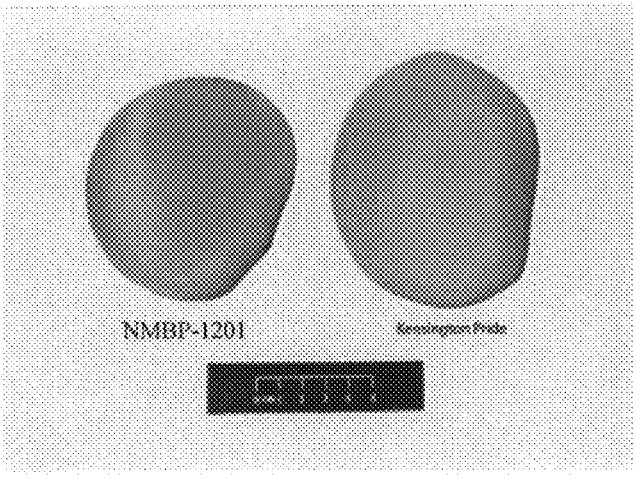

FIG. 8—illustrates a comparison of fruit from plants of the new variety with that of the 'Kensington Pride' variety.

Figure 9:
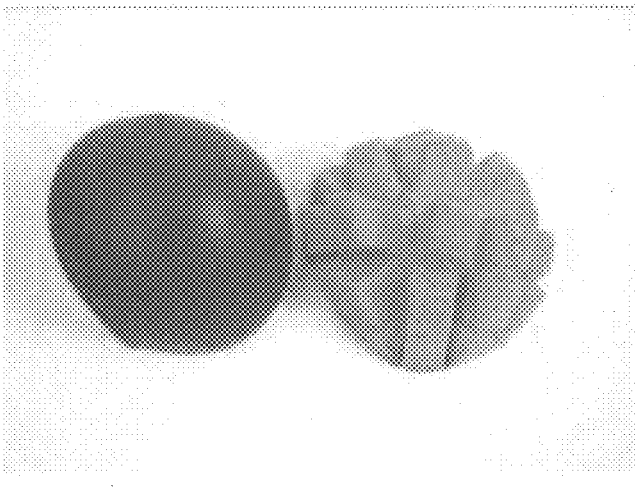

FIG. 9—illustrates specimens of ripe fruit, whole and flesh cut.

Figure 10:
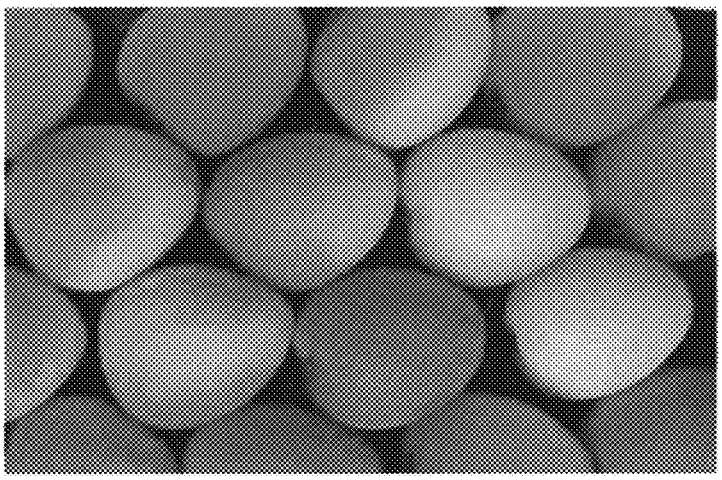

FIG. 10—illustrates specimens of ripe fruit.

Figure 11:
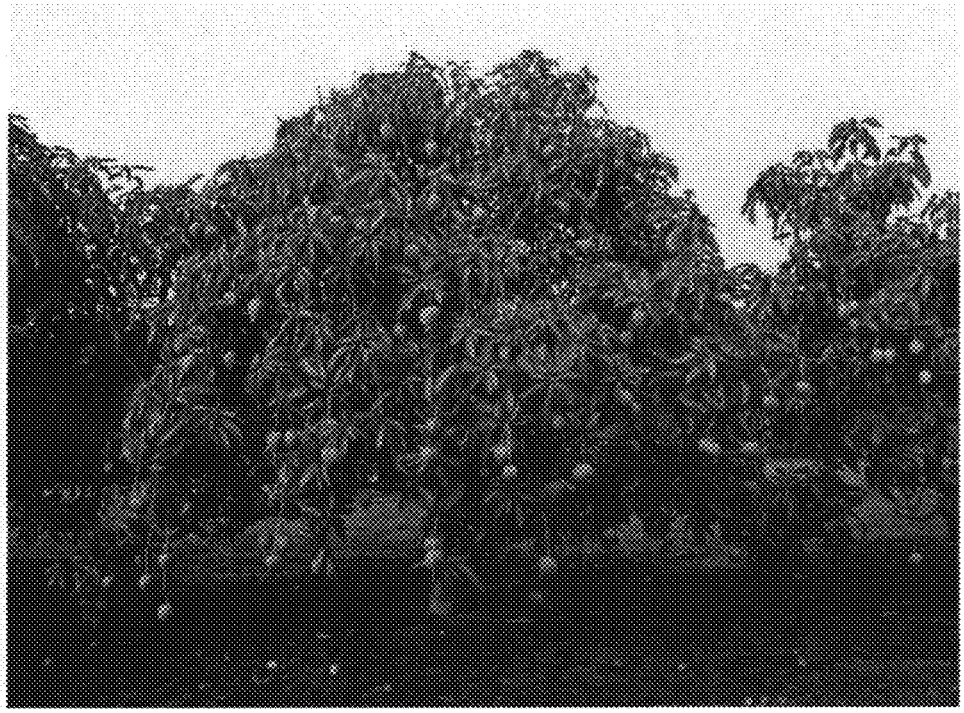

FIG. 11—illustrates a specimen of a single tree with mature fruit.

Figure 12:
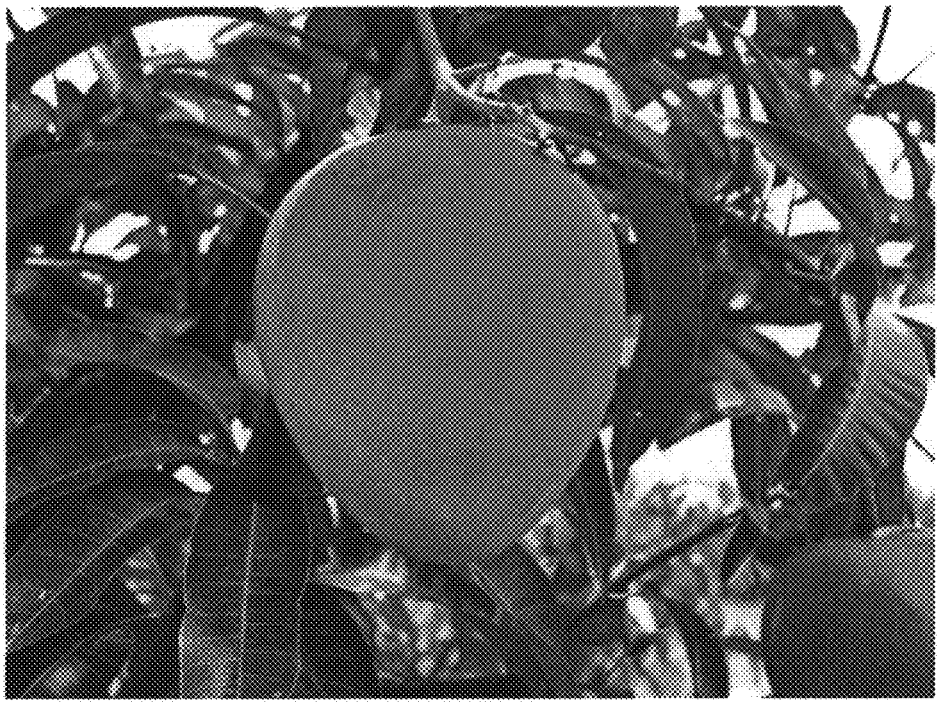

FIG. 12—illustrates a specimen of mature fruit ripening on a tree.

Figure 13:
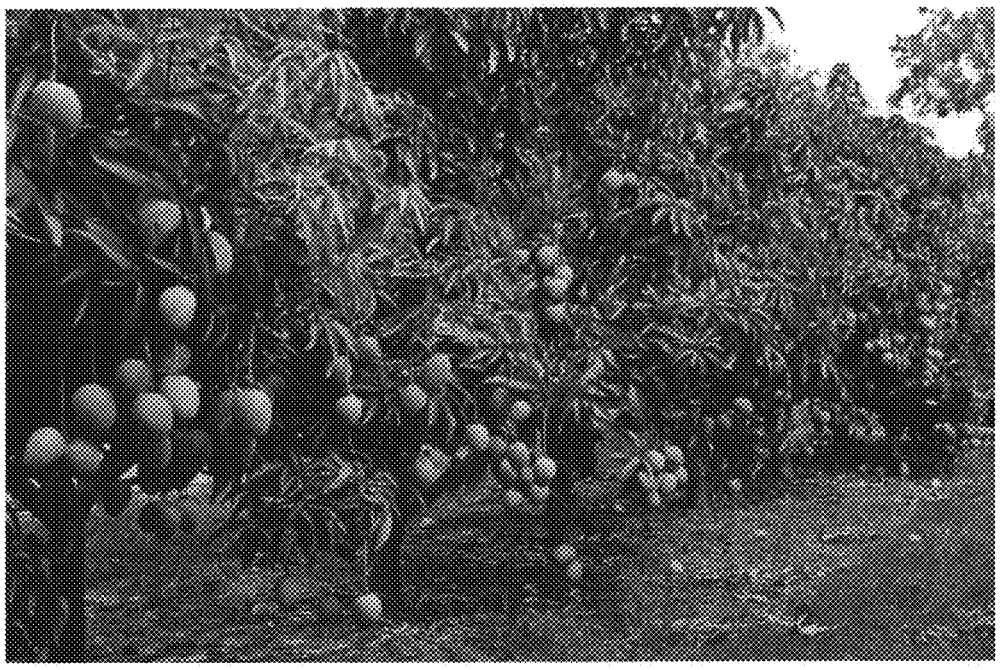

FIG. 13—illustrates specimens of trees with mature fruit.

Figure 14:
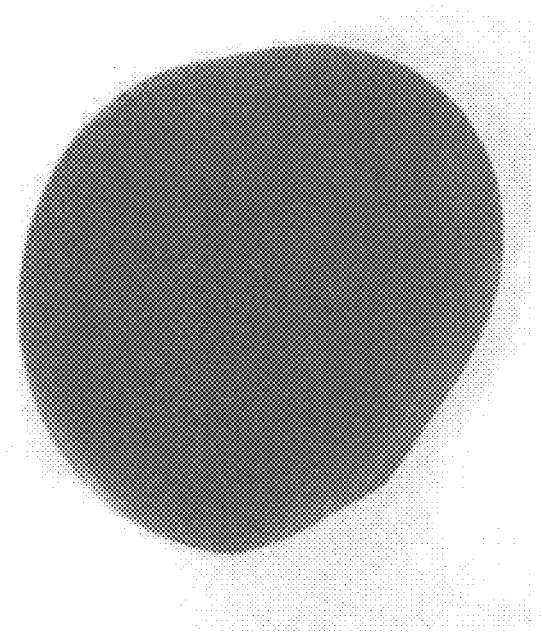

FIG. 14—illustrates a specimen of ripe fruit—side view.

Figure 15:
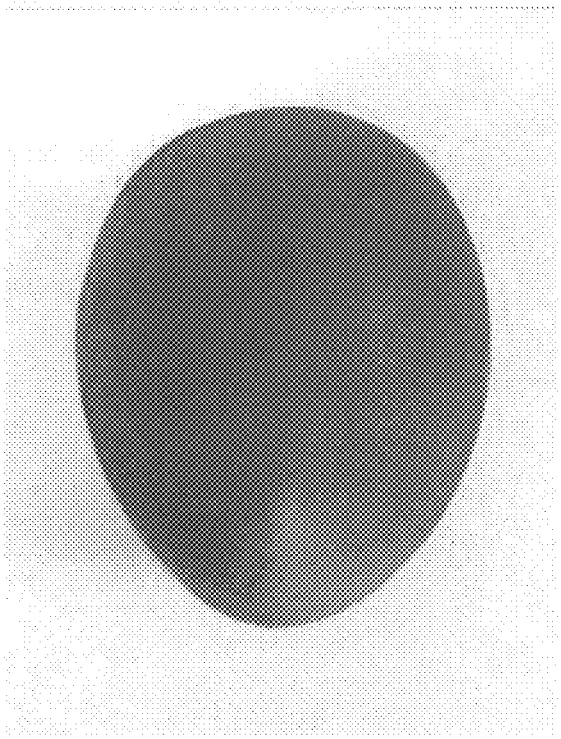

FIG. 15—illustrates a specimen of ripe fruit—front view.

Figure 16:
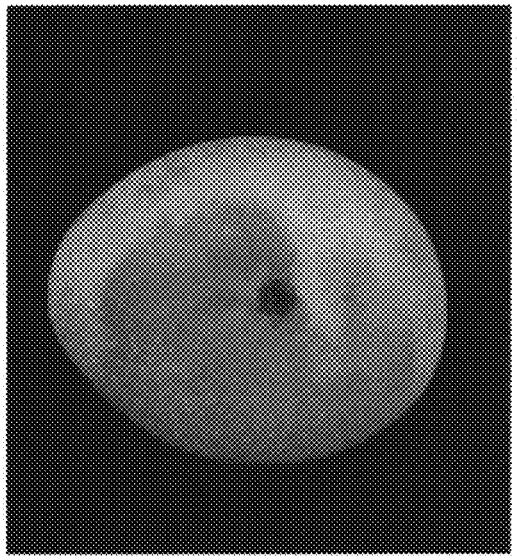

FIG. 16—illustrates a specimen of ripe fruit—top view—showing stalk attachment.

Figure 17:
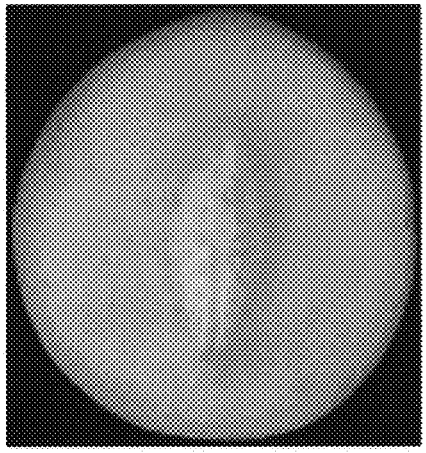

FIG. 17—illustrates a specimen of ripe fruit—halved—displaying flesh and endocarp.

DETAILED BOTANICAL DESCRIPTION

The chart used in the identification of colors is that of The Royal Horticultural Society ("R.H.S." Colour Chart), London, England, Fourth Edition, 2001. The terminology which precedes reference to the chart has been added to indicate the corresponding color in more common terms. The description is based on a trail design which was a randomized complete block design with five single 8-10 year old tree replicates in Queensland, Australia. 10 to 20 random measurements of each character were assessed on each of the five single tree replicates.

Plant:

a. *Vigor*.—Commonly medium to high vigor tree with a compact medium to dense canopy and the canopy shape is spreading.
b. *Attitude of main branches*.—Intermediate to spreading.
c. *Height*.—Commonly 4 to 6 m in 8 to 10-year-old trees under standard annual pruning.
d. *Width*.—Commonly 4 m in 8 to 10-year-old trees under standard annual pruning.
e. *Bark*.—Commonly no striation and medium rough; texture is smooth to medium texture; color is commonly near Grey-Brown Group 199A.

Leaves:

a. *Anthocyanin*.—Present with medium intensity on young leaves.
b. *Leaf blade*.—Size — Length is typically 217.62 mm±4.76 std. dev on average; width is typically 23.38 mm±4.77 std. dev. on average; and average length to width ratio is typically 4.13:1±1.77 std. dev. Shape — Generally elliptic with an acute base and attenuate apex; shape in cross section is concave. Color of lower surface of mature leaf — Commonly near Yellow-Green Group 146C. Color of upper surface of mature leaf — Commonly near Green Group 137C. Color of lower surface of immature leaf — Commonly near Greyed-Purple Group 187A. Color of upper surface of immature leaf — Commonly near Greyed-Purple Group 187B. Twisting — Present in some leaves, not all leaves. Spacing of secondary veins — Medium. Undulation of margin — Absent or weak. Serration — Absent. Venation — Pinnate with medium secondary veins which are approximately 10.49 mm±1.11 std. dev. apart, and the color is commonly near Yellow-Green Group 150C.

c. *Petiole*.—Attitude in relation to shoot — Semi erect to perpendicular. Length — Short, typically near 26.32 mm on average, commonly between 16-30 mm. Diameter — Commonly between 17-48 mm. Color — Commonly near Yellow-Green Group 145A.

Inflorescence:

a. *Length*.—Typically 315.94 mm±36.00 std. dev., on average.
b. *Width*.—Typically 193.31 mm±29.69 std. dev., on average.
c. *Ratio length to width*.—1.72:1±3.08 std. dev., on average.
d. *Number of inflorescence branches*.—17.84±3.08 std. dev., on average.
e. *Anthocyanin coloration of axis and branches*.—Strong.
f. *Flower diameter*.—Approximately 8.19 mm±0.62 std. dev., on average.
g. *Number of flowers per inflorescence*.—Commonly between 300 and 1500 on average.
h. *Pubescence on axis and branches*.—Commonly medium to sparse.
i. *Inflorescence type*.—Narrowly to broadly conical panicle.
j. *Color of inflorescence axis and branches*.—Commonly near Red-Purple Group 59C.
k. *Percentage of hermaphrodite flowers and male flowers pre inflorescence*.—Varies depending on temperature during inflorescence development.
l. *Horizontal attitude of axis*.—
m. *Color of petal pre-anthesis*.—Commonly near Yellow Group 2C.
n. *Color of sepal pre-anthesis*.—Commonly near Yellow Group 2C.
o. *Color of flower peduncle pre-anthesis*.—Commonly near Red-Purple Group 59C.
p. *Color of wilted petal post-anthesis*.—Commonly near Red-Purple Group 59A.
q. *Color of sepal post-anthesis*.—Commonly near Yellow Group 2C.
r. *Color of flower peduncle post-anthesis*.—Commonly near Red-Purple Group 59C.
s. *Anthocyanin coloration wilted petal post-anthesis*.—Present, intensity is strong.
t. *Fertile stamen(s)*.—Position in relation to style is parallel to oblique, length in relation to style is equal to longer; typically two.
u. *Pistil*.—Single.
v. *Staminodes*.—Typically 3 present.
w. *Filament and style*.—Color not observed.

Fruit:

a. *Mature fruit*.—Weight — Typically 245 to 530 g, approximately 361 g on average, and approximately 24% of fruit in the 460 to 540 g range. Size — Short to medium in length, medium to broad in width, with a small length/width ratio. Depth — Approximately 81.8 mm on average. Overall shape — Commonly ovate/round with a slight beak and a broad elliptic cross section. Stalk cavity — Absent or shallow. Presence of neck — Absent. Shape of ventral shoulder — Rounded upward. Shape of dorsal shoulder — Rounded downward. Length of groove in ventral shoulder — Absent or short. Depth of groove in ventral shoulder — Absent or shallow. Bulging on ventral shoulder — Absent. Presence of sinus — Absent. Bulging proximal of stylar scar — Absent or weak. Point at stylar scar — Medium. Diameter of stalk attachment — Medium. Roughness of surface — Absent. Skin coloration — Generally green with red blush and blush commonly near Red-Purple Group 60A. Lenticels — Small lenticels are sparsely present.
b. *Ripe fruit*.—Skin coloration — Commonly yellow background with soft red to dark red blush over 50% of the skin when grown in the sun, and fruit inside the canopy do not blush. Lenticels — Medium sized, medium density, and yellow in color. Thickness of skin — Thin to medium. Adherence of skin to flesh — Medium. Firmness — Soft to medium; similar to 'Delta R2E2' variety; and approximately 0.96 mm depression at 50 g for 30 sec on average. Texture of flesh — Fine to medium; soft. Amount of fiber attached to stone — Low to medium. Amount of fiber attached to skin — Low to medium. Flavor — Sweet rich 'Kensington Pride' variety style flavor with a slight tang, no turpentine flavor. Pulp color — Commonly near Yellow-Orange Group 17A. Pulp fiber — Low. Pulp depth — On a cut cheek is approximately 30 mm on average.
c. *Fruit count per panicle*.—Predominantly single fruit per panicle.
d. *Seed*.—Prominence of point at stylar area — Medium to strong. Relief of stone surface — Grooved. Sharp points on surface — Present. Fibres on cheeks of stone — Medium length and medium density. Texture of fibre — Fine to medium. Endocarp — Thick, color is not observed.

Development:

a. *Seed embryony*.—Polyembryonic.
b. *Time of beginning of flowering*.—Medium to late.
c. *Time of fruit maturity*.—Early to medium, varies with temperature; in Mareeba district of Queensland Australia the typical length of fruit maturing is between three months and three months, two weeks.
d. *Cropping*.—Seven-year-old trees in their fourth year of cropping yielded commonly yielded between 10 to 146 kg per tree in Kensington Pride rootstock.
e. *Harvest season*.—Commonly early to mid-season; and commonly between 'Kensington Pride' variety and 'R2E2' variety.
f. *Yield*.—Medium to heavy; commonly a tendency for biennial bearing.
g. *Hardiness*.—Coldest observed temperature withstood was 4° C.; hottest observed temperature withstood was 39° C.

h. *Bloom*.—Varies, typically between mid-July and late-September in Mareeba district of Queensland Australia.

i. *Pest/disease resistance*.—Not observed to date.

j. *Shipping quality, fruit storage life, fruit market use*.—Not observed to date.

Plants of the 'NMBP-1201' variety have not been observed under all possible environmental conditions to date. Accordingly, it is possible that the phenotypic expression may vary somewhat with changes in light intensity and duration, cultural practices, and other environmental conditions.

I claim:

1. A new and distinct Mango plant characterized by the following combination of characteristics:

(a) displays a medium vigor plant with a compact dense canopy, (b) exhibits a medium to heavy yielding with a tendency for biennial bearing, (c) is polyembryonic, (d) has a harvest season that is early to mid-season, and (e) provides a fruit with sweet Kensington Pride style flavor with a slight tang;

substantially as herein shown and described.

* * * * *